US008383776B2

(12) United States Patent
Bang

(10) Patent No.: US 8,383,776 B2
(45) Date of Patent: Feb. 26, 2013

(54) PURIFICATION OF FACTOR XIII POLYPEPTIDES FROM BIOLOGICAL MATERIALS

(75) Inventor: Susanne Bang, Bagsærd (DK)

(73) Assignee: Novo Nordisk Health Care AG, Zurich (CH)

( * ) Notice: Subject to any disclaimer, the term of this patent is extended or adjusted under 35 U.S.C. 154(b) by 175 days.

(21) Appl. No.: 12/838,593

(22) Filed: Jul. 19, 2010

(65) Prior Publication Data

US 2010/0297098 A1 Nov. 25, 2010

Related U.S. Application Data

(63) Continuation of application No. 11/661,524, filed as application No. PCT/EP2005/054207 on Aug. 26, 2005, now abandoned.

(60) Provisional application No. 60/606,026, filed on Aug. 31, 2004.

(30) Foreign Application Priority Data

Aug. 27, 2004 (DK) ................................ 2004 01301

(51) Int. Cl.
*A61K 35/14* (2006.01)
*A61K 38/36* (2006.01)
*C07K 14/745* (2006.01)
*C07K 1/18* (2006.01)
*C07K 1/20* (2006.01)

(52) U.S. Cl. ........ 530/381; 530/412; 530/415; 530/416; 530/417

(58) Field of Classification Search .................. None
See application file for complete search history.

(56) References Cited

U.S. PATENT DOCUMENTS

| | | | |
|---|---|---|---|
| 4,265,233 A | 5/1981 | Sugitachi et al. |
| 4,298,598 A | 11/1981 | Schwarz et al. |
| 4,362,567 A | 12/1982 | Schwarz et al. |
| 4,377,572 A | 3/1983 | Schwarz et al. |
| 4,414,976 A | 11/1983 | Schwarz et al. |
| 4,453,939 A | 6/1984 | Zimmerman et al. |
| 4,597,899 A | 7/1986 | Falke |
| 5,114,916 A | 5/1992 | Shirahata et al. |
| 5,204,447 A | 4/1993 | Bishop |
| 5,245,014 A | 9/1993 | Kaersgaard |
| 5,607,917 A | 3/1997 | Carter et al. |
| 5,612,456 A | 3/1997 | Bishop et al. |
| 7,008,926 B2 | 3/2006 | Bishop |
| 2004/0014657 A1 | 1/2004 | Ohrstrom et al. |
| 2007/0015709 A1 | 1/2007 | Ohrstrom et al. |
| 2007/0021340 A1 | 1/2007 | Ohrstrom et al. |

FOREIGN PATENT DOCUMENTS

| | | |
|---|---|---|
| CN | 1051732 | 5/1991 |
| EP | 268772 A2 | 6/1988 |
| GB | 2102811 A | 2/1983 |
| JP | 7-502734 | 3/1995 |
| JP | 7-506479 | 7/1995 |
| JP | 8-505129 | 6/1996 |
| WO | WO 90/05777 | 5/1990 |
| WO | WO 93/03147 | 2/1993 |
| WO | WO 93/12813 | 7/1993 |
| WO | WO 94/11022 | 5/1994 |
| WO | WO 02/36155 | 5/2002 |
| WO | WO 02/38167 | 5/2002 |
| WO | WO 02/067980 | 9/2002 |
| WO | WO 02/067981 | 9/2002 |
| WO | 2004/007533 A1 | 1/2004 |

OTHER PUBLICATIONS

De Backer-Royer et al., Purification and properties of factor XIII from human placenta, International Journal of Biochemistry, 1992, vol. 24, Issue 1, pp. 91-97.
Delbarre, F. et al, Factor XIII Treatment for Scleroderma, 1981, vol. 318, Issue 8239, pp. 204.
Greenberg, C.S et al. Journal of Biological Chemistry the Zymogen Forms of Blood . . . 1982 257—6096-6101.
Grivaux, M et al. Revue Pneumologie Clinique Carcinome Bronchiolo-Alveolaire . . . 1987 43—102-103, (abstract).
Guillevin, L. et al. Pharmatherapeutica Treatment of Progressive Systemic . . . 1985 4 2 76-80.
Henze, T A et al. Thrombosis and Haemostasis Factor XIII Concentrate for . . . 1987 58—No. 513.
Ichinose, A et al. Biochemistry Amino Acid Sequence of the B . . . 1986 25—4633-4638.
Ichinose, et al. Biochemistry Amino Acid Sequence of the A . . . 1986 25—6900-6906.
Kuratsuji, T et al. Haemostasis Factor XIII Dificiency in . . . 1982 11—229-234.
Suzuki, R et al. Thrombosis and Haemostasis Coagulation Findings in . . . 1987 58—No. 509.
Vogt, R.N. et al. Biochemical Journal the Metabolism of Nitrosothiols in the . . . 2003 374—657-666.
Wilhelm, B. et al, Transglutaminases: purification and activity assays, Journal of Chromatography, 1996, 163-177, vol. 684, Elsevier Science.
Ando, Y et al, High-performance Liquid Chromatographic Assay of Transglutaminase and Its Application to the Purification of Human Erythrocyte Transglutaminase and Platelet Factor XIII, J. Biochem, 1987, 1331-1337, vol. 101—No. 6, The British Library.
Bergamini, C. M. et al, Purification of Testicular Transglutaminase by Hydrophobic Chromatography on Phenyl-Sepharose, Biochemistry International, 1992, 557-565, vol. 27—No. 4, Academic Press Australia.
Bishop, P.D. et al, Expression Purification and Characterization of Human Factor XIII in *Saccharomyces cerevisiae*, Biochemistry, 1990, 1861-1869, vol. 29—No. 7.

(Continued)

*Primary Examiner* — Marsha Tsay
(74) *Attorney, Agent, or Firm* — Michael J. Brignati

(57) ABSTRACT

The invention relates to a method for purifying a factor XIII polypeptide from a biological material, the method comprising subjecting the material to sequential chromatography on an anion-exchange matrix and a hydrophobic interaction matrix.

8 Claims, No Drawings

OTHER PUBLICATIONS

Lai, T-S et al, Purification and Characterization of Recombinant Human Coagulation Factor XIII A-Chains Expressed in *E. coli*, Protein Expression and Purification, 1994, 125-132, vol. 5—No. 2, Academic Press Inc.

Arens, R.A.S. et al, Role of factor XIII in fibrin clot formation and effects of genetic polymorphisms, Blood, 2002, 743-754, vol. 100—No. 3, The American Society of Hematology.

Translation of JP Abstract JP 2004-123566, 2004.

Translation of JP Abstract JP 2-247199, 1990.

PURIFICATION OF FACTOR XIII POLYPEPTIDES FROM BIOLOGICAL MATERIALS

This application is a continuation of application Ser. No. 11/661,524 filed Feb. 27, 2007 which is a 35 U.S.C. §371 National Stage application of International Application PCT/EP2005/054207 (published as WO 2006/021584), filed Aug. 26, 2005, which claimed priority of Danish Patent Application PA 2004 01301, filed Aug. 27, 2004; this application claims priority under 35 U.S.C. §119 of U.S. Provisional Application 60/606,026, filed Aug. 31, 2004.

FIELD OF THE INVENTION

The present invention relates to methods of protein purification from biological materials, especially the purification of factor XIII and factor XIII polypeptides from biological fluids.

BACKGROUND OF THE INVENTION

The blood coagulation factor XIII (FXIII), the fibrin stabilising factor, is a transglutaminase that binds to and cross-links fibrin monomers in the haemostatic plug thereby providing a fibrin structure with increased mechanical strength and resistance against fibrinolysis (see Ariëns et al, Blood 100(3), 743-754 (2002)). Factor XIII is also known as "fibrinoligase" and "fibrin stabilizing factor". When activated, factor XIIIa is able to form intermolecular gamma-glutamyl-ε-lysine cross-links between side chains of fibrin molecules and other substrates. Factor XIII is found in plasma and in platelets. The enzyme exists in plasma as a tetrameric zymogen consisting of two A-subunits (also referred to as "a") and two B subunits (also referred to as "b") (this tetrameric zymogen is designated $A_2B_2$ (also referred to as "$a_2b_2$")) and in platelets as a zymogen consisting of two A-subunits (this dimeric zymogen is designated $A_2$-dimer (also referred to as "$a_2$-dimer")).

It has been described that factor XIII may be used for treating bleeding episodes, in patients having a congenital factor XIII deficiency as well as in patients not having a congenital factor XIII deficiency, see for instance U.S. Pat. No. 5,114,916, U.S. Pat. No. 5,607,917, WO 2002038167, WO 2002036155, WO 200267981, and WO 200267980.

U.S. Pat. No. 5,612,456 concerns the preparation of factor XIII from biological fluids using an acetate precipitation step in combination with anion-exchange chromatography and hydrophobic interaction chromatography.

SUMMARY OF THE INVENTION

The present invention concerns a method for purifying a factor XIII polypeptide from a biological material, the method comprising subjecting the material to sequential chromatography on an anion-exchange matrix and a hydrophobic interaction matrix. In one embodiment, the method for purifying a factor XIII polypeptide from a biological material does not comprise a precipitation step to produce a factor XIII-containing precipitate.

The present invention also concerns a method for purifying a factor XIII polypeptide from a biological material, the method comprising the step of subjecting the biological material to chromatography using a hydrophobic interaction chromatographic material, wherein said hydrophobic interaction chromatographic material is Phenyl Sepharose™ High Performance High Substitution from Amersham.

The present invention also concerns the use of polypeptides prepared by the above method for reducing blood loss.

DETAILED DESCRIPTION OF THE INVENTION

The present invention concerns a method for purifying a factor XIII polypeptide from a biological material, the method comprising subjecting the material to sequential chromatography on an anion-exchange matrix and a hydrophobic interaction matrix.

In one embodiment, the present invention concerns a method for purifying a factor XIII polypeptide from a biological material, the method comprising the steps of:

(a) subjecting a biological material comprising a factor XIII polypeptide to chromatography on a first anion-exchange chromatographic material, said chromatography comprising:
  (i) applying said biological material to said first anion-exchange chromatographic material;
  (ii) eluting unbound material from the first anion-exchange chromatographic material with a buffer A, which buffer A is suitable for eluting material not bound to the first anion-exchange chromatographic material; and
  (iii) eluting said factor XIII polypeptide from the first anion-exchange chromatographic material by gradient-elution with buffer A', which buffer A' is suitable for eluting said factor XIII polypeptide from said first anion-exchange chromatographic material;

(b) subjecting the eluate from step (iii) or a fluid prepared by use of the eluate from step (iii) to chromatography using a hydrophobic interaction chromatographic material, said chromatography comprising:
  (iv) applying the eluate from step (iii) or a fluid prepared by use of the eluate from step (iii) to said hydrophobic interaction chromatographic material;
  (v) eluting unbound material from the chromatographic material with buffer B, which buffer B is suitable for eluting material not bound to the hydrophobic interaction chromatographic material; and
  (vi) eluting said factor XIII polypeptide from said chromatographic material by gradient-elution with buffer B', which buffer B' is suitable for eluting factor XIII polypeptide from said hydrophobic interaction chromatographic material.

Purification of a factor XIII polypeptide is the process of increasing the concentration of the factor XIII polypeptide in a sample in relation to other components of said sample, resulting in an increase in the purity of the factor XIII polypeptide. It should be understood that the concentration of a factor XIII polypeptide in a sample in relation to other components of said sample is not equivalent to the concentration of factor XIII polypeptide in the sample. The increase in the purity of the factor XIII polypeptide may be followed measured by use of methods known in the art, such as for instance by use of SDS-PAGE (Sodium Dodecyl Sulfate Polyacrylamide Gel Electrophoresis), HPLC (High Performance Liquid Chromatography) or Berichrome assays (Dade Behring Diagnostics).

Factor XIII polypeptides include the complete factor XIII zymogen tetramer, the $A_2B_2$ intermediate and factor XIIIa as well as subunits thereof, including the A subunit and $A_2$ dimers, as well as naturally occurring allelic variants of factor XIII and genetically engineered variants of factor XIII that retain at least part of the characteristic cross-linking activity of factor XIII; an example of such a variant is the Val34Leu variant of wild-type human factor XIII (i.e. a variant in which the Val residue at position 34 in the amino acid sequence of wild-type human factor XIII is replaced by a Leu residue).

Derivatives and fragments of such polypeptides, where the derivatives and fragments have retained at least a significant part of the characteristic cross-linking activity of factor XIII, are also encompassed. The wild-type sequence of human factor XIII can be found in EP 268772 and EP 236978.

In one embodiment of the present invention, the factor XIII polypeptide is a recombinant factor XIII. In one embodiment of the present invention, the factor XIII polypeptide is human factor XIII. In one embodiment of the present invention, the factor XIII polypeptide is a dimer of A subunits. In one embodiment of the present invention, the factor XIII polypeptide is a dimer of human A subunits.

Biological material may be any material derived from or containing cells, cell components or cell products. A biological material may be a biological fluid.

A biological fluid may be any fluid derived from or containing cells, cell components or cell products. Biological fluids include, but are not limited to cell cultures, cell culture supernatants, cell lysates, cleared cell lysates, cell extracts, tissue extracts, blood, plasma, serum, all of which may also be homogenizates and filtrates, and fractions thereof, for instance collected by chromatography of unfractionated biological fluids.

The factor XIII polypeptides may be purified from a wide variety of biological materials, including lysates, homogenizates or extracts of cells which naturally produce a factor XIII polypeptide, but also of cells which have been genetically modified to produce a factor XIII polypeptide, such as yeast cells (for instance Saccharomyces cerevisiae cells) transformed with DNA coding for a factor XIII polypeptide.

The biological material may be treated by use of a number of methods prior to application on the first anion-exchange chromatographic material. Such methods include, but a not limited to, centrifugation, lysis, homogenization, and high pressure disruption. In one embodiment, the biological material is a biological fluid. In one embodiment of the present invention, the biological fluid is the supernatant of a cell lysate. In one embodiment of the present invention, the biological fluid is the supernatant of a yeast cell lysate.

In one embodiment of the present invention, the factor XIII polypeptide is purified from a cell culture, such as a yeast cell culture, as described above. Prior to the chromatography in step (a), the yeast cells may be lysed in a lysis buffer, and the resulting supernatant may be subjected to disruption by high pressure, such as for instance a pressure of about 2.0 kBar or below, such as a pressure of from about 1.0 kBar to about 2.0 kBar, such as at a pressure of about 1.5 kBar, optionally following a homogenisation step. In one embodiment of the present invention, the buffer used for lysing the cells is buffer A. The lysis buffer may comprise protease inhibitors such as EDTA (ethylenediamine tetraacetic acid), phenanthroline, pepstatin and particularly PMSF (phenyl methyl sulfonyl fluoride), but other commercially available protease inhibitors may also be used.

A buffer is a solution comprising a substance, which substance is capable of preventing significant changes in the pH of solutions to which small amounts of acids or bases are added and thereby of maintaining largely the original acidity or basicity of the solution. A buffer usually comprises a weak acid or weak base together with a salt thereof.

Prior to the chromatography in step (a), buffer A may be added to the biological material, for instance in the amount of about one volume, in the amount of about two volumes, in the amount of about three volumes, or in an amount of more than about three volumes. Buffer A may also be used to prepare the biological fluid, for instance by resuspending a pellet of cells in buffer A. In one embodiment, buffer A is used for lysing the cells.

The biological fluid is centrifuged, and may optionally also be filtered, prior to the chromatography in step (a).

The pH of the biological fluid may be adjusted to the pH of buffer A prior the chromatography in step (a), for instance by using 1 M HCl or 1 M NaOH or by other means known in the art.

The conductivity of the biological fluid may be adjusted to the conductivity of buffer A prior the chromatography in step (a), for instance by adding buffer A to the biological fluid or by other means known in the art.

The first anion-exchange chromatographic material may be any anion-exchange chromatographic material known in the art which is capable of binding a factor XIII polypeptide under one set of conditions and releasing it under a different set of conditions, such as an anion-exchange chromatographic material comprising a quaternary ammonium ion. Further non-limiting examples of anion-exchange chromatographic materials include derivatised dextrans, agarose, cellulose, polyacrylamide, and specialty silicas, such as PEI, DEAE, QAE and Q derivatives. Suitable anion-exchange chromatographic material may be identified by subjecting a biological fluid comprising factor XIII polypeptide to chromatography on the anion-exchange chromatographic material of choice, collecting fractions and determining the purity and content of the fractions, for instance by use of SDS-PAGE (Sodium Dodecyl Sulfate Polyacrylamide Gel Electrophoresis), HPLC (High Performance Liquid Chromatography) or Berichrome assays (Dade Behring Diagnostics), monitoring the absorbance of the eluate at 280 nm and by use of other methods known in the art. Examples of suitable anion-exchange chromatographic materials include, but are not limited to Source™ 30Q (Amersham Biosciences), Toyopearl® SuperQ-650M (Tosoh Bioscience), Q-sepharose™ (Amersham Biosciences) and DEAE Fast-Flow Sepharose (Amersham Biosciences). The first anion-exchange chromatographic material may be pre-equilibrated with buffer A prior to application of the biological material.

In one embodiment of the present invention, buffer A and/or buffer A' comprises one or more stabilizing agents which are capable of increasing the physical and/or chemical stability of the factor XIII polypeptide.

The term "physical stability" of the factor XIII polypeptide as used herein refers to the potential tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the factor XIII polypeptide when present in buffer A may be evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations may be performed in a sharp focused light with a dark background. The turbidity of the formulation may be characterized by a visual score ranking the degree of turbidity, for instance on a scale from 0 to 3 (a formulation showing no turbidity then corresponding to a visual score 0, and a formulation showing visual turbidity in daylight corresponding to visual score 3). A formulation is classified as physically unstable with respect to protein aggregation when it shows visual turbidity in daylight. Alternatively, the turbidity of the formulation may be evaluated by simple turbidity measurements well-known to the skilled person, for instance by measuring the optical density of the solution at a wavelength of 405 nm ($OD_{405}$). Physical stability of the aqueous protein formulations may also be evaluated by using a spectroscopic agent or probe of the conformational status of the protein. The probe is preferably a small molecule that preferentially binds to a non-native conformer of the protein. One example of a small-molecule spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the factor XIII polypeptide when present in buffer A as used herein refers to chemical covalent changes in the protein structure leading to formation of chemical degradation products with potentially lower biological potency and/or potentially increased immunogenic properties compared to the native protein structure. Various chemical degradation products can be formed depending on the type and nature of the native protein and the environment to which the protein is exposed. Elimination of chemical degradation can most probably not be completely avoided, and an increase in amounts of chemical degradation products is often seen during storage and use of the protein formulation, as well-known to a person skilled in the art. Most proteins are prone to deamidation, a process in which the side-chain amide group in glutaminyl or asparaginyl residues is hydrolysed to form a free carboxylic acid. Other degradation pathways involve formation of high-molecular-weight transformation products wherein two or more protein molecules are covalently bound to each other via transamidation and/or disulfide interactions, leading to formation of covalently bound dimer, oligomer and polymer degradation products (Stability of Protein Pharmaceuticals, Ahern. T. J. & Manning M. C., Plenum Press, New York 1992). Oxidation (e.g. of methionine residues) can be mentioned as another variant of chemical degradation. The chemical stability of the factor XIII polypeptide when present in buffer A can be evaluated by measuring the amounts of chemical degradation products at various times after exposure to different environmental conditions; the formation of degradation products can, for example, often be accelerated by increase in temperature. The amount of each individual degradation product is often determined by separation of the degradation products depending on molecule size and/or charge using various chromatographic techniques (e.g. SEC-HPLC and/or RP-HPLC).

Any agent which is capable of significantly improving the physical and/or chemical stability of factor XIII polypeptide when present in buffer A (e.g. as determined by measuring turbidity at $OD_{405}$ over a period of time) may be used as a stabilizing agent in buffer A or buffer A'.

An agent suitable for use as stabilizing agent in buffer A may, for instance, be a salt (e.g. sodium chloride), a sugar, an alcohol (such as an $C_3$-$C_8$ alcohol), an alditol, an amino acid (e.g. glycine, L-histidine, arginine, lysine, isoleucine, aspartic acid, tryptophan or threonine), a polyethyleneglycol (e.g. PEG400), or a mixture of one or more thereof. Any sugar, such as a mono-, di-, or polysaccharide, or a water-soluble glucan, may be used. An alditol is a polyalcohol of structure $HOCH_2$—$[CH(OH)]_n$—$CH_2OH$, where n is 0, 1, 2, 3 . . . etc. Non-limiting examples of substances which are sugars, alcohols or alditols are fructose, glucose, mannose, sorbose, xylose, maltose, lactose, sucrose, trehalose, dextran, pullulan, dextrin, cyclodextrin, soluble starch, hydroxyethyl starch, carboxymethylcellulose-Na, mannitol, sorbitol, inositol, galactitol, dulcitol, xylitol, arabitol, glycerol (glycerine), propan-1,2-diol (propylene glycol), propan-1,3-diol, and butan-1,3-diol. The sugars, alcohols and alditols mentioned above may be used individually or in combination. There is no fixed limit to the amount used, as long as the substance is soluble in the liquid preparation and improves the physical stability of a factor XIII polypeptide in solution. In this respect, reference is made to Remington: The Science and Practice of Pharmacy, 19th edition, 1995.

In one embodiment of the present invention, buffer A comprises one or more stabilizing agents of the polyalcohol type.

In one embodiment of the present invention, buffer A comprises one or more stabilizing agents selected from the group consisting of glycerol (propan-1,2,3-triol), propylene glycol (propan-1,2-diol), propan-1,3-diol, propyl alcohol (1-propanol) and isopropyl alcohol (2-propanol). In one embodiment of the present invention, buffer A comprises one or more stabilizing agents selected from the group consisting of glycerol, propylene glycol and propan-1,3-diol. In one embodiment of the present invention, buffer A comprises propylene glycol.

In a further embodiment of the present invention, when the stabilizing agent in buffer A is a liquid alcohol or liquid polyalcohol [such as, e.g., glycerol, propylene glycol, propan-1,3-diol, propyl alcohol or isopropyl alcohol], the stabilizing agent is present in a concentration of from about 5% by volume (v/v) to about 50% (v/v). In a further embodiment, a stabilizing agent of the liquid alcohol or liquid polyalcohol type in buffer A is present in a concentration of from about 10% (v/v) to about 50% (v/v). In a further embodiment, a stabilizing agent of the liquid alcohol or liquid polyalcohol type in buffer A is present in a concentration of from about 10% (v/v) to about 20% (v/v). In a further embodiment, a stabilizing agent of the liquid alcohol or liquid polyalcohol type in buffer A is present in a concentration of about 10% (v/v). In a still further embodiment, a stabilizing agent of the liquid alcohol or liquid polyalcohol type in buffer A is present in a concentration of about 20% (v/v).

Buffer A may comprise protease inhibitors such as EDTA (ethylenediamine tetraacetic acid), phenanthroline, pepstatin and particularly PMSF (phenyl methyl sulfonyl fluoride), but other commercially available protease inhibitors may also be used.

In one embodiment of the present invention, the pH of buffer A is between 6.5 and 9. In a further embodiment, the pH of buffer A is between 7 and 9. In a further embodiment, the pH of buffer A is about 8.

In one embodiment of the present invention, the conductivity of buffer A is less than about 2 mS/cm.

Buffer A' is used for the elution of the factor XIII polypeptide by gradient-elution. Gradient elution means that the composition of buffer A' is changed during the course of elution. Typically, the concentration of one or more of the components of the buffer used for washing in step (ii), in this case buffer A, is increased or decreased during the course of elution or a new component is added to the buffer, and the concentration of this component is then increased during the course of elution. This increase or decrease may take place continuously or in discrete steps as it is known in the art. For elution of material bound to an anion-exchange chromatographic material, it is customary to add a salt, for instance NaCl, to buffer A, creating buffer A', and then increase the concentration of the salt until at least the majority of the bound factor XIII polypeptide is eluted. The determination of which fractions containing factor XIII polypeptide to pool for further processing, for instance to exclude undesired impurities eluting at the beginning or the end of the factor XIII polypeptide elution, is within the knowledge of a person skilled in the art. Likewise, the general art of performing an anion-exchange chromatography with regard to for instance pre-equilibration, elution time, washing, reconstitution of the anion-exchange chromatographic material etc is well-known.

After eluting the factor XIII polypeptide in step (iii), the eluate containing the factor XIII polypeptides is taken to step (iv) without an intervening step involving precipitation of factor XIII polypeptide. It may be that some factor XIII polypeptide precipitates depending on the handling and treatment of the eluate, however, no steps to intentionally precipitate a factor XIII polypeptide should be taken. Other intervening steps may be contemplated. The eluate may also be kept at, for instance, 4° C. for 24 hours or longer, or at, for instance, −80° C.

The hydrophobic interaction chromatographic material for use in step (b) may be any hydrophobic interaction chromatographic material known in the art, which is capable of binding a factor XIII polypeptide under one set of conditions and releasing it under a different set of conditions, such as a hydrophobic interaction chromatographic material derivatised with phenyl, butyl or octyl groups, or polyacrylic resins. Non-limiting examples of suitable hydrophobic interaction chromatographic material are Amberchrom™ CG 71 (Tosoh Bioscience), Phenyl Sepharose™ High Performance (Amersham, cat no 17-1082), Phenyl Sepharose™ 6 Fast Flow High Substitution (Amersham, cat no 17-0973), Toyopearl® Butyl 650 (Tosoh Bioscience), Toyopearl® Phenyl (Tosoh Bioscience), Source™ 15Phe (Amersham, cat no 17-0147), Butyl Sepharose™ High Performance High Substitution (Amersham, cat no 17-3100), Octyl-Sepharose™ (Amersham, cat no 17-0946) and Phenyl Sepharose™ High Performance High Substitution (Amersham), and the like. In one embodiment of the present invention, the hydrophobic interaction chromatographic material uses phenyl as a ligand.

Buffer B may be added to the eluate from stage (iii) or a fluid prepared by use of the eluate from stage (iii) prior to the chromatography in step (b) in an amount of about one to three volumes or more, or a concentrated version of buffer B, comprising the same ingredients as buffer B, but in, e.g., four times the concentration, is added to the eluate from stage (iii) or a fluid prepared by use of the eluate from stage (iii) in an amount corresponding to the strength of the concentrated buffer (a twice-concentrated buffer is added in the amount of one volume). The pH is then adjusted to the pH of buffer B.

Buffer B may comprise protease inhibitors such as EDTA (ethylenediamine tetraacetic acid), phenanthroline, pepstatin and particularly PMSF (phenyl methyl sulfonyl fluoride), but other commercially available protease inhibitors may also be used.

Buffer B may have a pH from about 6 to about 8, for instance about 7.5. In one embodiment of the present invention, buffer B has a conductivity of more than 25 mS/cm. In another embodiment of the invention, buffer B has a conductivity of at most 50 mS/cm. This may be achieved, for example, by use of a phosphate buffer or by other means known in the art. In one embodiment of the present invention, the conductivity of the eluate from step (iii), or of a fluid prepared by use of the eluate from step (iii), is adjusted to a conductivity of at least about 25 mS/cm.

Buffer B' is used for the elution of the factor XIII polypeptide by gradient elution. In gradient elution, the composition of buffer B' is changed during the course of elution. Typically, the concentration of one or more of the components of the buffer used for washing in step (v), in this case buffer B, is increased or decreased during the course of elution, or a new component is added to the buffer and the concentration of this component is then increased during the course of elution. This increase or decrease may take place continuously or in discrete steps, as is well known in the art. For elution of material bound to a hydrophobic interaction chromatographic material, it is customary to dilute the washing buffer with water until at least a major portion of the bound factor XIII polypeptide is eluted. The determination of which fractions containing factor XIII polypeptide to pool for further processing, e.g. in order to exclude undesired impurities eluting at the beginning or the end of the factor XIII polypeptide elution, is within the knowledge of a person skilled in the art. Likewise, the general art of performing a hydrophobic interaction chromatography with regard to, e.g., pre-equilibration, elution time, washing, reconstitution of the hydrophobic interaction chromatographic material, etc., is well known.

In one embodiment of the present invention, the eluate from stage (vi) or a fluid prepared by use of the eluate from stage (vi) is treated by use of a method comprising a step of
(1) addition of one or more stabilizing agents which are capable of increasing the stability of the factor XIII polypeptide in an amount effective to significantly improve the stability thereof, and/or
(2) adjusting the pH of the eluate from stage (vi), or a fluid prepared by use of the eluate from stage (vi), to a pH between about 7 and about 8.

These steps, and optionally other steps of post-processing known in the art, may be carried out alone or in combination, and the order in which the steps are performed is not critical. The person skilled in the art will be able to determine how and when to perform these steps.

The stabilizing agent mentioned in step (1) should be capable of increasing the physical and/or chemical stability, as described above, of the factor XIII polypeptide. Any agent which is capable of significantly improving the physical and/or chemical stability of factor XIII polypeptide (e.g. as determined by measuring turbidity at $OD_{405}$ over a period of time) may be used as a stabilizing agent in step (1).

An agent suitable for use as stabilizing agent in step (1) may, for instance, be a salt (e.g. sodium chloride), a sugar, an alcohol (such as an $C_3$-$C_8$ alcohol), an alditol, an amino acid (e.g. glycine, L-histidine, arginine, lysine, isoleucine, aspartic acid, tryptophan or threonine), a polyethyleneglycol (e.g. PEG400), or a mixture of one or more thereof. Any sugar, such as a mono-, di-, or polysaccharide, or a water-soluble glucan, may be used. Non-limiting examples of substances which are sugars, alcohols or alditols are fructose, glucose, mannose, sorbose, xylose, maltose, lactose, sucrose, trehalose, dextran, pullulan, dextrin, cyclodextrin, soluble starch, hydroxyethyl starch, carboxymethylcellulose-Na, mannitol, sorbitol, inositol, galactitol, dulcitol, xylitol, arabitol, glycerol (glycerine), propan-1,2-diol (propylene glycol), propan-1,3-diol, and butan-1,3-diol. The sugars, alcohols and alditols mentioned above may be used individually or in combination.

There is no fixed limit to the amount used, as long as the substance is soluble in the liquid preparation and improves the physical stability of a factor XIII polypeptide in solution. In this respect, reference is made to Remington: The Science and Practice of Pharmacy, 19th edition, 1995.

In one embodiment of the present invention, the stabilizing agent used in step (1) is a polyalcohol.

In one embodiment of the present invention, the stabilizing agent used in step (1) is selected from the group consisting of glycerol (propan-1,2,3-triol), propylene glycol (propan-1,2-diol), propan-1,3-diol, propyl alcohol (1-propanol) and isopropyl alcohol (2-propanol). In one embodiment of the present invention, the stabilizing agent used in step (1) is selected from the group consisting of glycerol, propylene glycol and propan-1,3-diol. In one embodiment of the present invention, the stabilizing agent used in step (1) is propylene glycol.

In a further embodiment of the present invention, when the stabilizing agent used in step (1) is a liquid alcohol or liquid polyalcohol [such as, e.g., glycerol, propylene glycol, propan-1,3-diol, propyl alcohol or isopropyl alcohol], it is added to a concentration of from about 5% (v/v) to about 50% (v/v). In a further embodiment, a stabilizing agent of the liquid alcohol or liquid polyalcohol type used in step (1) is added to a concentration of from about 10% (v/v) to about 50% (v/v). In a further embodiment, a stabilizing agent of the liquid alcohol or liquid polyalcohol type used in step (1) is added to a concentration of from about 10% (v/v) to about 20% (v/v). In a further embodiment, a stabilizing agent of the liquid alcohol or liquid polyalcohol type used in step (1) is added to a concentration of about 10% (v/v). In a still further embodiment, a stabilizing agent of the liquid alcohol or liquid polyalcohol type used in step (1) is added to a concentration of about 20% (v/v).

In one embodiment of the present invention, the stabilizing agent(s) used in step (1) is/are the same as the stabilizing agent(s) used in buffer A. In a further embodiment of the present invention, the stabilizing agent(s) is/are added to a concentration similar to the concentration of the stabilizing agent(s) used in buffer A.

In one embodiment of the present invention, the pH in step (2) is adjusted to about 7.5.

After eluting the factor XIII polypeptide in step (vi), the eluate containing the factor XIII polypeptide should not be subjected to a precipitation step. It is possible that some factor XIII polypeptide precipitates, depending on the handling and further treatment of the eluate, but no steps to intentionally precipitate a factor XIII polypeptide should be taken. Other intervening steps may be contemplated. The eluate may also be kept at, e.g., 4° C. for 24 hours or longer, or at, e.g., −80° C.

In one embodiment of the present invention, the method further comprises a step of subjecting the eluate from stage (vi), or a fluid prepared by use of the eluate from stage (vi), to chromatography on a second anion-exchange chromatographic material, said chromatography comprising:

(vii) applying the eluate from stage (vi), or a fluid prepared by use of the eluate from stage (vi), to said second anion-exchange chromatographic material;

(viii) eluting unbound material from the second anion-exchange chromatographic material with buffer C, which buffer C is suitable for eluting material not bound to the second anion-exchange chromatographic material; and (ix) eluting said factor XIII polypeptide from the second anion-exchange chromatographic material with buffer C', which buffer C' is suitable for eluting factor XIII polypeptides which bind to the second anion-exchange chromatographic material in step (viii).

A fluid prepared by use of the eluate from stage (vi) may, for instance, be prepared by use of a method comprising one or both of steps (1) and (2) as described above.

In one embodiment of the present invention, the conductivity of the eluate from stage (vi), or a fluid prepared by use of the eluate from stage (vi), is adjusted to less than about 2 mS/cm.

The components of buffer C and buffer C' may be chosen with a view to the desired final pharmaceutical composition of the factor XIII polypeptide. Such considerations are within the knowledge of a person skilled in the art.

In one embodiment of the present invention, buffer C comprises one or more stabilizing agents, which stabilizing agents are capable of increasing the physical and/or chemical stability, as described above, of the factor XIII polypeptide. Any agent which is capable of significantly improving the physical and/or chemical stability of factor XIII polypeptide when present in buffer C (e.g. as determined by measuring turbidity at $OD_{405}$ over a period of time) may be used as a stabilizing agent in buffer C or buffer C'.

An agent suitable for use as stabilizing agent in buffer C may, for instance, be a salt (e.g. sodium chloride), a sugar, an alcohol (such as an $C_3$-$C_8$ alcohol), an alditol, an amino acid (e.g. glycine, L-histidine, arginine, lysine, isoleucine, aspartic acid, tryptophan or threonine), a polyethyleneglycol (e.g. PEG400), or a mixture of one or more thereof. Any sugar, such as a mono-, di-, or polysaccharide, or a water-soluble glucan, may be used. Non-limiting examples of substances which are sugars, alcohols or alditols are fructose, glucose, mannose, sorbose, xylose, maltose, lactose, sucrose, trehalose, dextran, pullulan, dextrin, cyclodextrin, soluble starch, hydroxyethyl starch, carboxymethylcellulose-Na, mannitol, sorbitol, inositol, galactitol, dulcitol, xylitol, arabitol, glycerol (glycerine), propan-1,2-diol (propylene glycol), propan-1,3-diol, and butan-1,3-diol. The sugars, alcohols and alditols mentioned above may be used individually or in combination. There is no fixed limit to the amount used, as long as the substance is soluble in the liquid preparation and improves the physical stability of a factor XIII polypeptide in solution. In this respect, reference is made to Remington: The Science and Practice of Pharmacy, 19th edition, 1995.

In one embodiment of the present invention, buffer C comprises one or more stabilizing agents of the polyalcohol type.

In one embodiment of the present invention, buffer C comprises one or more stabilizing agents selected from the group consisting of glycerol (propan-1,2,3-triol), propylene glycol (propan-1,2-diol), propan-1,3-diol, propyl alcohol (1-propanol) and isopropyl alcohol (2-propanol). In one embodiment of the present invention, buffer C comprises one or more stabilizing agents selected from the group consisting of glycerol, propylene glycol and propan-1,3-diol. In one embodiment of the present invention, buffer C comprises propylene glycol.

In a further embodiment of the present invention, when the stabilizing agent in buffer C is a liquid alcohol or liquid polyalcohol [such as, e.g., glycerol, propylene glycol, propan-1,3-diol, propyl alcohol or isopropyl alcohol], it is present in a concentration of from about 5% (v/v) to about 50% (v/v). In a further embodiment, a stabilizing agent of the liquid alcohol or liquid polyalcohol type in buffer C is present in a concentration of from about 10% (v/v) to about 50% (v/v). In a further embodiment, a stabilizing agent of the liquid alcohol or liquid polyalcohol type used in buffer C is present in a concentration of from about 10% (v/v) to about 20% (v/v). In a further embodiment, a stabilizing agent of the liquid alcohol or liquid polyalcohol type in buffer C is present in a concentration of about 10% (v/v). In a still further embodiment, a stabilizing agent of the liquid alcohol or liquid polyalcohol type in buffer C is present in a concentration of about 20% (v/v).

In one embodiment of the present invention, buffer C comprises the same stabilizing agent(s) as used in buffer A. In a further embodiment of the present invention, buffer C comprises the stabilizing agent(s) in a concentration similar to the concentration of the stabilizing agent(s) in buffer A.

If a lyophilized formulation of a factor XIII polypeptide is considered, then buffer C and/or buffer C' should comprise, for example, sucrose or mannitol or one or more other ingredients suitable for lyophilization instead of, for example, propylene glycol.

Buffer C' is used for the elution of the factor XIII polypeptide by gradient elution, wherein the composition of buffer C' is changed during the course of elution. Buffer C' is typically derived from the buffer used for washing in step (viii), in this case buffer C, in that the concentration of one or more of the components of the latter buffer is increased or decreased during the course of elution, or a new component is added to the latter buffer and the concentration of this component is then increased during the course of elution. This increase or decrease may take place continuously or in discrete steps, as is well known in the art. For elution of material bound to an anion-exchange chromatographic material, buffer C' is typically derived from buffer C by addition thereto of a salt, e.g. NaCl, the concentration of the salt then being increased until at least a major portion of the bound factor XIII polypeptide is eluted. The determination of which fractions containing factor XIII polypeptide to pool for further processing, e.g. in order to exclude undesired impurities eluting at the beginning or the end of the factor XIII polypeptide elution, is within the knowledge of a person skilled in the art. Likewise, the general art of performing an anion-exchange chromatography with regard to, e.g., pre-equilibration, elution time, washing, reconstitution of the anion-exchange chromatographic material, etc., is well known.

The conductivity and pH, as well as other parameters of the eluate comprising factor XIII polypeptide, may be adjusted after elution by means known in the art.

In one embodiment of the present invention, the method further comprises a step of subjecting the eluate from stage (vi), or a fluid prepared by use of the eluate from stage (vi), to ultrafiltration in a manner known in the art.

In one embodiment of the present invention, the method further comprises a step of subjecting the eluate from stage (vi), or a fluid prepared by use of the eluate from stage (vi), to diafiltration in a manner known in the art.

In one embodiment of a method according to the present invention, the method does not comprise a precipitation step to produce a factor XIII polypeptide-containing precipitate. It is possible that some factor XIII polypeptide precipitates, depending on the handling and treatment of the fluid containing the factor XIII polypeptide, but no steps to intentionally precipitate a factor XIII polypeptide should be taken.

The present invention provides a pharmaceutical composition comprising a factor XIII polypeptide prepared by use of a method according to the present invention. In one embodiment, such a pharmaceutical composition has a pH from about 2.0 to about 10.0. The pharmaceutical composition may further comprise a buffer system, preservative(s), tonicity-adjusting agent(s), chelating agent(s), stabilizer(s) and/or surfactant(s). In one embodiment of the present invention the pharmaceutical composition is an aqueous formulation, i.e. a formulation comprising liquid water. Such a formulation is typically a solution or a suspension. In a further embodiment of the present invention the pharmaceutical composition is an aqueous solution. The term "aqueous formulation" as employed in the context of the present invention refers to a formulation comprising at least 50% by weight (w/w) of water. Likewise, the term "aqueous solution" refers to a solution comprising at least 50% (w/w) water, and the term "aqueous suspension" refers to a suspension comprising at least 50% (w/w) water.

In one embodiment, the factor XIII polypeptide in a pharmaceutical composition of the invention in the form of an aqueous formulation is present in a concentration from about 0.2 mg/ml to about 30 mg/ml, such as from about 0.2 mg/ml to about 10 mg/ml, e.g. from about 0.5 mg/ml to about 10 mg/ml, for instance from about 1 mg/ml to about 10 mg/ml.

In one embodiment, the pharmaceutical composition is a dried formulation (e.g. a freeze-dried or spray-dried formulation) intended for reconstitution by the physician or the patient by addition of solvents and/or diluents prior to use.

In one embodiment, the present invention relates to a pharmaceutical composition comprising an aqueous solution of a factor XIII polypeptide prepared by use of a method according to the present invention, together with a buffer, wherein said formulation has a pH from about 2.0 to about 10.0.

In one embodiment of the present invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the present invention the buffer is selected from the group consisting of acetate buffers, carbonate buffers, citrate buffers, glycylglycine buffers, histidine buffers, glycine buffers, lysine buffers, arginine buffers, phosphate buffers (containing, e.g., sodium dihydrogen phosphate, disodium hydrogen phosphate or trisodium phosphate), TRIS [tris(hydroxymethyl)aminomethane] buffers, bicine buffers, tricine buffers, malate buffers, succinate buffers, maleate buffers, fumarate buffers, tartrate buffers, aspartate buffers, and mixtures thereof.

In one embodiment of the present invention the formulation further comprises a pharmaceutically acceptable preservative. In a further embodiment of the present invention the preservative is selected from the group consisting of phenol, o-cresol, m-cresol, p-cresol, chlorocresol, methyl p-hydroxybenzoate, ethyl p-hydroxybenzoate, propyl p-hydroxybenzoate, butyl p-hydroxybenzoate, 2-phenoxyethanol, 2-phenylethanol, benzyl alcohol, chlorobutanol, thiomerosal, bronopol, benzoic acid, imidurea, chlorohexidine, sodium dehydroacetate, benzethonium chloride, chlorphenesine (3-p-chlorphenoxypropane-1,2-diol) and mixtures thereof. In a further embodiment of the present invention the preservative is present in a concentration from 0.1 mg/ml to 20 mg/ml. In one further embodiment of the present invention the preservative is present in a concentration from 0.1 mg/ml to 5 mg/ml. In another further embodiment of the present invention the preservative is present in a concentration from 5 mg/ml to 10 mg/ml. In another further embodiment of the present invention the preservative is present in a concentration from 10 mg/ml to 20 mg/ml. The use of a preservative in pharmaceutical compositions is well-known to the skilled person (see, e.g., Remington: *The Science and Practice of Pharmacy*, 19th edition, 1995).

In one embodiment of the present invention the formulation further comprises an tonicity-adjusting agent (normally incorporated for the purpose of rendering the formulation substantially isotonic). In a further embodiment of the present invention the tonicity-adjusting agent is selected among salts (e.g. sodium chloride), sugars, alcohols (such as $C_3$-$C_8$ alcohols), alditols, amino acids (e.g. glycine, L-histidine, arginine, lysine, isoleucine, aspartic acid, tryptophan or threonine), polyethyleneglycols (e.g. PEG400), and mixtures thereof. Any sugar, such as a mono-, di-, or polysaccharide, or a water-soluble glucan, may be used. Non-limiting examples of substances which are sugars, alcohols or alditols are fructose, glucose, mannose, sorbose, xylose, maltose, lactose, sucrose, trehalose, dextran, pullulan, dextrin, cyclodextrin, soluble starch, hydroxyethyl starch, carboxymethylcellulose-Na, mannitol, sorbitol, inositol, galactitol, dulcitol, xylitol, arabitol, glycerol (glycerine), propan-1,2-diol (propylene glycol), propan-1,3-diol, and butan-1,3-diol. The sugars, alcohols and alditols mentioned above may be used individually or in combination. There is no fixed limit to the amount used, as long as the substance is soluble in the liquid preparation.

In one embodiment, the tonicity-adjusting agent is present in a concentration of from about 1 mg/ml to about 150 mg/ml. In a further embodiment of the present invention, the tonicity-adjusting agent is present in a concentration of from about 1 mg/ml to about 50 mg/ml. In another embodiment of the present invention, the tonicity-adjusting agent is present in a concentration of from about 1 mg/ml to about 7 mg/ml. In another further embodiment of the present invention, the tonicity-adjusting agent is present in a concentration of from about 8 mg/ml to about 24 mg/ml. In another further embodiment of the present invention, the tonicity-adjusting agent is present in a concentration of from about 25 mg/ml to about 50 mg/ml. The use of an tonicity-adjusting agent in pharmaceutical compositions is well-known to the skilled person (see, e.g., Remington: *The Science and Practice of Pharmacy*, 19th edition, 1995).

In one embodiment of the present invention the formulation further comprises a chelating agent. In a further embodiment of the present invention the chelating agent is selected from salts of EDTA, citric acid and aspartic acid, and mixtures thereof. In a further embodiment of the present invention the chelating agent is present in a concentration from 0.1 mg/ml to 5 mg/ml. In one further embodiment of the present invention the chelating agent is present in a concentration from 0.1 mg/ml to 2 mg/ml. In another further embodiment of the present invention the chelating agent is present in a concentration from 2 mg/ml to 5 mg/ml. The use of a chelating agent in pharmaceutical compositions is well-known to the skilled person (see, e.g., Remington: *The Science and Practice of Pharmacy,* 19th edition, 1995).

The pharmaceutical compositions of the present invention include as a therapeutically active component a polypeptide that possibly may exhibit aggregate formation during storage in liquid pharmaceutical compositions. The term "aggregate formation" is intended to indicate a physical interaction between the polypeptide molecules that results in formation of oligomers which may remain soluble, or of large visible aggregates that precipitate from the solution. The term "during storage" refers to a liquid pharmaceutical composition or formulation which, once prepared, is not immediately administered to a subject. Rather, following preparation, it is packaged for storage in a liquid form, in a frozen state, or in a dried form for later reconstitution into a liquid form or other form suitable for administration to a subject. The term "dried form" refers to a liquid pharmaceutical composition or formulation dried by freeze-drying [i.e. lyophilization; see, for example, Williams and Polli (1984), J. Parenteral Sci. Technol. 38:48-59], by spray-drying [see Masters (1991) in *Spray-Drying Handbook* (5th ed; Longman Scientific and Technical, Essex, U.K.), pp. 491-676; Broadhead et al. (1992) Drug Devel. Ind. Pharm. 18:1169-1206; and Mumenthaler et al. (1994) Pharm. Res. 11:12-20] or by air-drying [Carpenter and Crowe (1988), Cryobiology 25:459-470; and Roser (1991) Biopharm. 4:47-53]. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems, such as blockage of tubing, membranes or pumps when the polypeptide-containing pharmaceutical composition is administered using an infusion system.

In one embodiment of the present invention, the pharmaceutical composition comprises an amount of an amino acid base sufficient to decrease aggregate formation by the polypeptide during storage of the composition. The term "amino acid base" indicates an amino acid or a combination of amino acids where any given amino acid is present either in its free base form or in its salt form. When a combination of amino acids is used, all of the amino acids may be present in their free base forms, all may be present in their salt forms, or some may be present in their free base forms while others are present in their salt forms. In one embodiment, amino acids for use in preparing compositions of the present invention are those carrying a charged side chain, such as arginine, lysine, aspartic acid or glutamic acid. Any stereoisomer (i.e., L or D) of a particular amino acid (methionine, histidine, arginine, lysine, isoleucine, aspartic acid, tryptophan, threonine and mixtures thereof), or combinations of these stereoisomers or glycine or an organic base such as, but not limited to, imidazole, may be present in the pharmaceutical compositions of the present invention so long as the particular amino acid or organic base is present either in its free base form or its salt form. In one embodiment the L-stereoisomer of an amino acid is used. Compositions of the present invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the present invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. The compound imidazole is also to be regarded as an amino acid analogue in the context of the present invention.

In one embodiment of the present invention the amino acids or amino acid analogues are used in a concentration which is sufficient to prevent or delay aggregation of the protein.

In one embodiment, a pharmaceutical composition of the present invention comprises methionine (or another sulfur-containing amino acid or amino acid analogue) to inhibit oxidation of methionine residues to their sulfoxide form when the factor XIII polypeptide is a polypeptide comprising at least one methionine residue susceptible to such oxidation. The term "inhibit oxidation" is intended to indicate minimization of accumulation of oxidized species (of methionine) with time. Inhibition of methionine oxidation results in greater retention of the polypeptide in its proper molecular form. Any stereoisomer of methionine (L or D isomer) or combinations thereof can be used. The amount to be added should be an amount sufficient to inhibit oxidation of the methionine residues such that the amount of sulfoxide form of methionine is acceptable to regulatory agencies. Typically, this means that the composition contains no more than from about 10% to about 30% methionine sulfoxide form. This can in general be achieved by adding methionine in an amount such that the molar ratio of added methionine to methionine residues ranges from about 1:1 to about 1000:1, such as 10:1 to about 100:1.

In one embodiment of the present invention the pharmaceutical composition further comprises a stabilizer. The use of a stabilizer in pharmaceutical compositions is well known to the skilled person (see, e.g., Remington: *The Science and Practice of Pharmacy*, 19th edition, 1995). In one embodiment of the present invention the pharmaceutical composition comprises a stabilizer selected from high-molecular-weight polymers or from low-molecular-weight compounds. In a further embodiment, the stabilizer is selected from polyethylene-glycols (e.g. PEG 3350), polyvinyl alcohol (PVA), polyvinylpyrrolidone, carboxy/hydroxycellulose and derivatives thereof (including HPC, HPC-SL, HPC-L and HPMC), cyclodextrins, sulfur-containing substances as monothioglycerol, thioglycolic acid and 2-methylthioethanol, various salts (e.g. sodium chloride), glycerol, propylene glycol, propan-1,3-diol, propyl alcohol (1-propanol) and isopropyl alcohol (2-propanol).

A pharmaceutical composition of the present invention may also comprise additional stabilizing agents which further enhance stability of a therapeutically active polypeptide therein. Stabilizing agents of particular interest in relation to the present invention include, but are not limited to, methionine and EDTA, which protect the polypeptide against methionine oxidation, and a nonionic surfactant, which protects the polypeptide against aggregation associated with freeze-thawing or mechanical shearing.

In one embodiment of the present invention the pharmaceutical composition or formulation further comprises a surfactant. In a further embodiment the surfactant is selected from detergents, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives ("Tweens", e.g. Tween-20, Tween-40, Tween-80 and Brij-35), monoglycerides and ethoxylated derivatives thereof, diglycerides and polyoxyethylene derivatives thereof, alcohols, glycerol, lectins and phospholipids (eg. phosphatidyl-serine, phosphatidyl-choline, phosphatidyl-ethanolamine, phosphatidyl-inositol, diphosphatidyl-glycerol and sphingomyelin), derivatives of phospholipids (e.g. dipalmitoyl-phosphatidic acid) and lysophospholipids (e.g. palmitoyl lysophosphatidyl-L-serine and 1-acyl-sn-glycero-3-phosphate esters of ethanolamine, choline, serine or threonine), and alkyl-, alkoxyl-(alkyl ester) and alkoxy-(alkyl ether) derivatives of lysophosphatidyl and phosphatidylcholines, e.g. lauroyl and myristoyl derivatives of lysophosphatidylcholine, dipalmitoylphosphatidylcholine, and modifications of the polar head group, i.e. cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyranoside), sphingoglycolipids (e.g. ceramides, gangliosides), dodecylphosphocholine, hen egg lysolecithin, fusidic acid derivatives (e.g. sodium tauro-dihydrofusidate etc.), long-chain fatty acids [e.g. $C_6$-$C_{12}$ fatty acids (such as oleic acid or caprylic acid)] and salts thereof, acylcarnitines and derivatives thereof, $N^\alpha$-acylated derivatives of lysine, arginine and histidine, side-chain acylated derivatives of lysine and arginine, $N^\alpha$-acylated derivatives of dipeptides comprising any combination of lysine, arginine and histidine and a neutral or acidic amino acid, $N^\alpha$-acylated derivatives of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid and derivatives thereof, bile acids and salts thereof, and glycine or taurine conjugates, ursodeoxycholic acid, sodium cholate, sodium deoxycholate, sodium taurocholate, sodium glycocholate, N-hexadecyl-N,N-dimethyl-3-ammonio-1-propanesulfonate, anionic (alkyl-aryl-sulfonates) monovalent surfactants, zwitterionic surfactants (e.g. N-alkyl-N,N-dimethylammonio-1-propanesulfonates, 3-cholamido-1-propyldimethylammonio-1-propane-sulfonate), cationic surfactants (quaternary ammonium bases; e.g. cetyl-trimethylammonium bromide, cetylpyridinium chloride), non-ionic surfactants (eg. Dodecyl β-D-glucopyranoside), and poloxamines (eg. Tetronic's), i.e. tetrafunctional block copolymers derived from sequential addition of propylene oxide and ethylene oxide to ethylenediamine; or the surfactant may be selected from the group of imidazoline derivatives, or mixtures thereof.

The use of a surfactant in pharmaceutical compositions is well-known to the skilled person (see, e.g., Remington: *The Science and Practice of Pharmacy*, 19th edition, 1995).

Other ingredients may also be incorporated in a pharmaceutical composition of the present invention. Such additional ingredients may include wetting agents, emulsifiers, antioxidants, bulking agents, tonicity modifiers (tonicity-adjusting agents), chelating agents, metal ions, oleaginous vehicles, proteins (e.g. human serum albumin, gelatin or other proteins) and zwitterionic substances (e.g. betaine, taurine or an amino acid such as arginine, glycine, lysine or histidine). Such additional ingredients should not, of course, adversely affect the overall stability of the pharmaceutical composition of the present invention.

Pharmaceutical compositions containing a factor XIII polypeptide prepared by use of a method according to the present invention according to the present invention may be administered to a patient in need of such treatment by several different routes, e.g. topically (such as by application to the skin or to a mucous membrane), by routes which bypass absorption (such as administration in an artery, in a vein or in the heart), and by routes which involve absorption (such as by administration in the skin, beneath the skin, in muscle or in the abdomen).

Administration of pharmaceutical compositions according to the present invention to patients in need thereof may be via various routes of administration, e.g. lingual, sublingual, buccal, oral, in the stomach or intestine, nasal, pulmonary (e.g. via the bronchioles and alveoli or both), epidermal, dermal, transdermal, vaginal, rectal, ocular (e.g. via the conjunctiva), urethral or parenteral.

Pharmaceutical compositions of the present invention may be administered in various dosage forms, e.g. as solutions, suspensions, emulsions, microemulsions, multiple emulsion, foams, salves, pastes, plasters, ointments, tablets, coated tablets, rinses, capsules (e.g. hard gelatin capsules or soft gelatin capsules), suppositories, rectal capsules, drops, gels, sprays, powder, aerosols, inhalants, eye drops, ophthalmic ointments, ophthalmic rinses, vaginal pessaries, vaginal rings, vaginal ointments, injection solutions, in situ transforming solutions (e.g. in situ gelling, in situ setting, in situ precipitating or in situ crystallizing), infusion solution, or as implants.

Pharmaceutical compositions of the present invention may further be compounded in, or bound or conjugated to (e.g. via covalent, hydrophobic or electrostatic interactions), a drug carrier, drug delivery system or advanced drug delivery system in order to further enhance stability of the factor XIII polypeptide, to increase bioavailability, to increase solubility, to decrease adverse effects, to achieve chronotherapy well known to those skilled in the art, and/or to increase patient compliance. Examples of carriers, drug delivery systems and advanced drug delivery systems include, but are not limited to, polymers, e.g. cellulose and derivatives thereof, other polysaccharides (e.g. dextran and derivatives thereof, starch and derivatives thereof), poly(vinyl alcohol), acrylate and methacrylate polymers, polylactic acid and polyglycolic acid and block co-polymers thereof, polyethyleneglycols, carrier proteins (e.g. albumin), gels (e.g. thermogelling systems, such as block co-polymeric systems well known to those skilled in the art), micelles, liposomes, microspheres, nanoparticulates, liquid crystals and dispersions thereof, L2 phase and dispersions thereof well known to those skilled in the art of phase behaviour in lipid-water systems, polymeric micelles, multiple emulsions (self-emulsifying and self-microemulsifying), cyclodextrins and derivatives thereof, and dendrimers.

Pharmaceutical compositions comprising a factor XIII polypeptide prepared by use of a method according to the present invention are suitable for use in the formulation of solids, semisolids, powders and solutions for pulmonary administration using, for example, a metered dose inhaler, dry powder inhaler or a nebulizer, all of which are devices well known to those skilled in the art.

Pharmaceutical compositions comprising a factor XIII polypeptide prepared by use of a method according to the present invention are suitable for use in the formulation of controlled-release, sustained-release, protracted-release, retarded-release or slow-release drug delivery systems. Pharmaceutical compositions comprising a factor XIII polypeptide prepared by use of a method according to the present invention are, for instance, useful in formulation of parenteral controlled-release and sustained-release systems (both systems leading to a many-fold reduction in number of administrations) of types well known to those skilled in the art, such as controlled-release and sustained-release systems for subcutaneous administration. Without limiting the scope of the present invention, examples of useful controlled-release systems and compositions are hydrogels, oleaginous gels, liquid crystals, polymeric micelles, microspheres and nanoparticles, Methods for producing controlled release systems useful for pharmaceutical compositions comprising a factor XIII polypeptide prepared by use of a method according to the present invention include, but are not limited to, crystallization, condensation, co-crystallization, precipitation, co-precipitation, emulsification, dispersion, high-pressure homogenisation, encapsulation, spray-drying, microencapsulation, coacervation, phase separation, solvent evaporation to produce microspheres, extrusion and supercritical fluid processes. General reference is made to *Handbook of Pharmaceutical Controlled Release* (Wise, D. L., ed., Marcel Dekker, New York, 2000) and to *Drugs and the Pharmaceutical Sciences* vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, for example a syringe in a device of the pen type. Alternatively, parenteral administration can be performed by means of an infusion pump. A further option for administration of a composition in the form of a solution or suspension containing a factor XIII polypeptide prepared by use of a method according to the present invention is administration as a nasal or pulmonary spray. As another option, pharmaceutical compositions containing a factor XIII polypeptide prepared by use of a method according to the present invention may be adapted to transdermal administration, e.g. by needleless injection, by application of a patch (such as an iontophoretic patch) or by transmucosal (e.g. buccal) administration.

In one embodiment of the present invention, a pharmaceutical composition comprising a factor XIII polypeptide prepared by use of a method according to the present invention is stable for more than 6 weeks of usage and for more than 3 years of storage.

In another embodiment of the present invention, a pharmaceutical composition comprising a factor XIII polypeptide prepared by use of a method according to the present invention is stable for more than 4 weeks of usage and for more than 3 years of storage.

In a further embodiment of the present invention, a pharmaceutical composition comprising a factor XIII polypeptide prepared by use of a method according to the present invention is stable for more than 4 weeks of usage and for more than 2 years of storage.

In an still further embodiment of the present invention, a pharmaceutical composition comprising a factor XIII polypeptide prepared by use of a method according to the present invention is stable for more than 2 weeks of usage and for more than 2 years of storage.

The present invention also relates to a method for treating bleeding episodes, which method comprises administration of a pharmaceutical composition comprising an effective amount of a factor XIII polypeptide prepared by use of a method according to the present invention to a subject in need thereof.

In another aspect, the present invention relates to a method for reducing clotting time in a subject, which method comprises administration of a pharmaceutical composition comprising an effective amount of a factor XIII polypeptide prepared by use of a method according to the present invention to a subject in need thereof.

In a further aspect, the present invention relates to a method for prolonging the clot lysis time in mammalian plasma, which method comprises administration of a pharmaceutical composition comprising an effective amount of a factor XIII polypeptide prepared by use of a method according to the present invention to a subject in need thereof.

In another aspect, the present invention relates to a method for increasing clot strength in mammalian plasma, which method comprises administration of a pharmaceutical composition comprising an effective amount of a factor XIII polypeptide prepared by use of a method according to the present invention to a subject in need thereof.

In a further aspect, the present invention relates to a method for enhancing fibrin clot formation in mammalian plasma, which method comprises administration of a pharmaceutical composition comprising an effective amount of a factor XIII polypeptide prepared by use of a method according to the present invention to a subject in need thereof.

In another aspect, the present invention relates to a method for prevention of intraventricular haemorrhage in premature infants, which method comprises administration of a pharmaceutical composition comprising an effective amount of a factor XIII polypeptide prepared by use of a method according to the present invention to a subject in need thereof.

In a further aspect, the present invention relates to a method for reducing surgery-related blood loss in a subject during or after surgery, which method comprises administration of a pharmaceutical composition comprising an effective amount of a factor XIII polypeptide prepared by use of a method according to the present invention to a subject in need thereof.

In another aspect, the present invention relates to a method for treating hemophilia A, which method comprises administration of a pharmaceutical composition comprising an effective amount of a factor XIII polypeptide prepared by use of a method according to the present invention to a subject in need thereof.

In a further aspect, the present invention relates to a method for treating hemophilia B, which method comprises administration of a pharmaceutical composition comprising an effective amount of a factor XIII polypeptide prepared by use of a method according to the present invention to a subject in need thereof.

In another aspect, the present invention relates to a method for treating platelet disorders, which method comprises administration of a pharmaceutical composition comprising an effective amount of a factor XIII polypeptide prepared by use of a method according to the present invention to a subject in need thereof.

In a further aspect, the present invention relates to a method for treating von Willebrand's disease, which method comprises administration of a pharmaceutical composition comprising an effective amount of a factor XIII polypeptide prepared by use of a method according to the present invention to a subject in need thereof.

In a further embodiment of these methods, a factor XIII polypeptide prepared by use of a method according to the present invention is administered in combination with an effective amount of a factor VIIa polypeptide as described in WO200185198. In a further embodiment, the factor VIIa polypeptide and the factor XIII polypeptide prepared by use of a method according to the present invention are the sole active agents administered to the subject for the indicated treatment. In one embodiment, the factor XIII polypeptide prepared by use of a method according to the present invention and the factor VIIa polypeptide are administered simultaneously and in one-dosage form. In another embodiment, the factor XIII polypeptide prepared by use of a method according to the present invention and the factor VIIa polypeptide are administered sequentially. In a further embodiment, the factor XIII polypeptide prepared by use of a method according to the present invention and the factor VIIa polypeptide are administered within about 1-2 hours of each other, for example within 30 minutes of each other, for instance within 10 minutes of each other. The factor VIIa polypeptide and the factor XIII polypeptide may be provided, e.g., in the form of a kit comprising a factor XIII polypeptide prepared by use of a method according to the present invention in a first unit-dosage form and a factor VIIa polypeptide in a second unit-dosage form. In one embodiment, the effective amount of factor XIII polypeptide is from 0.05 mg/day to 500 mg/day (for a subject weighing 70 kg). In one embodiment, the effective amount of factor VIIa polypeptide is from 0.05 mg/day to 500 mg/day (70-kg subject).

In one embodiment, the subject to be treated is a human; in another embodiment, the subject has an impaired thrombin production; in one embodiment, the subject has a lowered plasma concentration of fibrinogen (e.g., in the case of a multi-transfused subject).

In the context of the present invention, an "effective amount" of a factor VIIa polypeptide and an "effective amount" of a factor XIII polypeptide are defined as the amount of factor VIIa polypeptide and factor XIII polypeptide, respectively, that is sufficient to prevent or reduce bleeding or blood loss, so as to cure, alleviate or partially arrest the disease and its complications alone or in combination with other administered therapeutic agents.

The present invention also relates to the use of a factor XIII polypeptide prepared by use of a method according to the present invention for treating bleeding episodes.

In another aspect, the present invention relates to the use of a factor XIII polypeptide prepared by use of a method according to the present invention for reducing clotting time in a subject.

In a further aspect, the present invention relates to the use of a factor XIII polypeptide prepared by use of a method according to the present invention for prolonging the clot lysis time in mammalian plasma.

In another aspect, the present invention relates to the use of a factor XIII polypeptide prepared by use of a method according to the present invention for increasing clot strength in mammalian plasma.

In a further aspect, the present invention relates to the use of a factor XIII polypeptide prepared by use of a method according to the present invention for enhancing fibrin clot formation in mammalian plasma.

In another aspect, the present invention relates to the use of a factor XIII polypeptide prepared by use of a method according to the present invention for prevention of intraventricular haemorrhage in premature infants.

In a further aspect, the present invention relates to the use of a factor XIII polypeptide prepared by use of a method according to the present invention for reducing surgery-related blood loss in a patient during or after surgery.

In another aspect, the present invention relates to the use of a factor XIII polypeptide prepared by use of a method according to the present invention for treating hemophilia A.

In a further aspect, the present invention relates to the use of a factor XIII polypeptide prepared by use of a method according to the present invention for treating hemophilia B.

In another aspect, the present invention relates to the use of a factor XIII polypeptide prepared by use of a method according to the present invention for treating platelet disorders.

In a further aspect, the present invention relates to the use of a factor XIII polypeptide prepared by use of a method according to the present invention for treating von Willebrand's disease.

The present invention also relates to the use of a factor XIII polypeptide prepared by use of a method according to the present invention for the preparation of a medicament for treating bleeding episodes.

In another aspect, the present invention relates to the use of a factor XIII polypeptide prepared by use of a method according to the present invention for the preparation of a medicament for reducing clotting time in a subject.

In a further aspect, the present invention relates to the use of a factor XIII polypeptide prepared by use of a method according to the present invention for the preparation of a medicament for prolonging the clot lysis time in mammalian plasma.

In another aspect, the present invention relates to the use of a factor XIII polypeptide prepared by use of a method according to the present invention for the preparation of a medicament for increasing clot strength in mammalian plasma.

In a further aspect, the present invention relates to the use of a factor XIII polypeptide prepared by use of a method according to the present invention for the preparation of a medicament for enhancing fibrin clot formation in mammalian plasma.

In another aspect, the present invention relates to the use of a factor XIII polypeptide prepared by use of a method according to the present invention for the preparation of a medicament for prevention of intraventricular haemorrhage in premature infants.

In a further aspect, the present invention relates to the use of a factor XIII polypeptide prepared by use of a method according to the present invention for the preparation of a medicament for reducing surgery-related blood loss in a patient during or after surgery.

In another aspect, the present invention relates to the use of a factor XIII polypeptide prepared by use of a method according to the present invention for the preparation of a medicament for treating hemophilia A.

In a further aspect, the present invention relates to the use of a factor XIII polypeptide prepared by use of a method according to the present invention for the preparation of a medicament for treating hemophilia B.

In another aspect, the present invention relates to the use of a factor XIII polypeptide prepared by use of a method according to the present invention for the preparation of a medicament for treating platelet disorders.

In a further aspect, the present invention relates to the use of a factor XIII polypeptide prepared by use of a method according to the present invention for the preparation of a medicament for treating von Willebrand's disease.

In one embodiment, the mammalian plasma referred to in certain aspects of the invention as described above is human plasma. In another embodiment, the mammalian plasma is normal plasma; in a further embodiment, the plasma is normal human plasma; in another embodiment, the mammalian plasma is plasma from a subject (e.g. a human subject) having an impaired thrombin generation. In a still further embodiment, the mammalian plasma is from a subject (e.g. a human subject) having a lowered concentration of fibrinogen.

In a further aspect of the invention, the factor XIII polypeptide in question prolongs the in vitro clot lysis time in normal human plasma.

A list of embodiments of the present invention is given below:

Embodiment 1

A method for purifying a factor XIII polypeptide from a biological material, the method comprising subjecting the material to sequential chromatography on an anion-exchange matrix and a hydrophobic interaction matrix.

Embodiment 2

A method according to embodiment 1, wherein the factor XIII polypeptide is a recombinant factor XIII.

Embodiment 3

A method according to embodiment 1 or embodiment 2, wherein the factor XIII polypeptide is human factor XIII.

Embodiment 4

A method according to embodiment 1 or embodiment 2, wherein the factor XIII polypeptide is a dimer of A subunits.

Embodiment 5

A method according to embodiment 4, wherein the factor XIII polypeptide is a dimer of human A subunits.

Embodiment 6

A method according to any of embodiments 1 to 5, wherein the biological material is a biological fluid.

Embodiment 7

A method according to embodiment 6, wherein the biological fluid is the supernatant of a cell lysate.

Embodiment 8

A method according to embodiment 7, wherein the biological fluid is the supernatant of a yeast cell lysate.

Embodiment 9

A method according to any of embodiments 1 to 8, wherein the method comprises the steps of:
(a) subjecting a biological material comprising a factor XIII polypeptide to chromatography on a first anion-exchange chromatographic material, said chromatography comprising:
  (i) applying said biological material to said first anion-exchange chromatographic material;
  (ii) eluting unbound material from the first anion-exchange chromatographic material with a buffer A, which buffer A is suitable for eluting material not bound to the first anion-exchange chromatographic material; and
  (iii) eluting said factor XIII polypeptide from the first anion-exchange chromatographic material by gradient-elution with buffer A', which buffer A' is suitable for eluting said factor XIII polypeptide from said first anion-exchange chromatographic material;
(b) subjecting the eluate from step (iii), or a fluid prepared by use of the eluate from step (iii), to chromatography using a hydrophobic interaction chromatographic material, said chromatography comprising:
  (iv) applying the eluate from step (iii), or a fluid prepared by use of the eluate from step (iii), to said hydrophobic interaction chromatographic material;
  (v) eluting unbound material from the chromatographic material with buffer B, which buffer B is suitable for eluting material not bound to the hydrophobic interaction chromatographic material; and
  (vi) eluting said factor XIII polypeptide from said chromatographic material by gradient-elution with buffer B', which buffer B' is suitable for eluting factor XIII from said hydrophobic interaction chromatographic material.

Embodiment 10

A method according to embodiment 9, wherein buffer A comprises one or more stabilizing agents which are capable of increasing the stability of the factor XIII polypeptide.

Embodiment 11

A method according to embodiment 10, wherein buffer A comprises a stabilizing agent, which stabilizing agent is a sugar, an alcohol or an alditol.

Embodiment 12

A method according to embodiment 11, wherein buffer A comprises a stabilizing agent, which stabilizing agent is a sugar, a $C_3$-$C_8$-alcohol or an alditol.

Embodiment 13

A method according to embodiment 12, wherein buffer A comprises a stabilizing agent, which stabilizing agent is a polyalcohol.

Embodiment 14

A method according to embodiment 12, wherein buffer A comprises a stabilizing agent selected from the group consisting of glycerol, propylene glycol, propan-1,3-diol, propyl alcohol and isopropyl alcohol.

Embodiment 15

A method according to embodiment 14, wherein buffer A comprises a stabilizing agent selected from the group consisting of glycerol, propylene glycol and propan-1,3-diol.

Embodiment 16

A method according to any of embodiments 13 to 15, wherein said stabilizing agent is present in a concentration of from about 5% (v/v) to about 50% (v/v).

Embodiment 17

A method according to embodiment 16, wherein said stabilizing agent is present in a concentration of from about 10% (v/v) to about 50% (v/v).

Embodiment 18

A method according to embodiment 17, wherein said stabilizing agent is present in a concentration of from about 10% (v/v) to about 20% (v/v).

Embodiment 19

A method according to embodiment 18, wherein said stabilizing agent is present in a concentration of about 10% (v/v).

Embodiment 20

A method according to embodiment 18, wherein said stabilizing agent is present in a concentration of about 20% (v/v).

Embodiment 21

A method according to any of embodiments 9 to 20, wherein the pH of buffer A is between about 6.5 and about 9.

Embodiment 22

A method according to embodiment 21, wherein the pH of buffer A is between about 7 and about 9.

Embodiment 23

A method according to embodiment 22, wherein the pH of buffer A is about 8.

Embodiment 24

A method according to any of embodiments 9 to 23, wherein buffer A has a conductivity of less than about 2 mS/cm.

Embodiment 25

A method according to any one of embodiments 9 to 24, wherein no precipitation to form a crystalline precipitate of the factor XIII polypeptide is performed between step (iii) and step (iv).

Embodiment 26

A method according to embodiment 25, wherein no precipitation step using sodium acetate to form a crystalline precipitate of the factor XIII polypeptide is performed between step (iii) and step (iv).

Embodiment 27

A method according to any of embodiments 1 to 26, wherein the hydrophobic interaction chromatographic material uses phenyl as the ligand.

Embodiment 28

A method according to embodiment 27, wherein the hydrophobic interaction chromatographic material is Source™ 15Phe.

Embodiment 29

A method according to embodiment 27, wherein the hydrophobic interaction chromatographic material is Phenyl Sepharose™ 6 Fast Flow High Substitution.

Embodiment 30

A method according to embodiment 27, wherein the hydrophobic interaction chromatographic material is Phenyl Sepharose™ High Performance High Substitution.

Embodiment 31

A method according to any of embodiments 9 to 30, wherein the pH of buffer B is from about 6 to about 8.

Embodiment 32

A method according to embodiment 31, wherein the pH of buffer B is about 7.5.

Embodiment 33

A method according to any of embodiments 9 to 32, wherein buffer B has a conductivity of more than 25 mS/cm.

Embodiment 34

A method according to embodiment 33, wherein buffer B has a conductivity of at most 50 mS/cm.

Embodiment 35

A method according to any of embodiments 9 to 34, wherein the eluate from stage (vi), or a fluid prepared by use of the eluate from stage (vi), is treated by use of a method comprising a step of
(1) addition of one or more stabilizing agents which are capable of increasing the stability of the factor XIII polypeptide in an amount effective to significantly improve the stability thereof, and/or
(2) adjusting the pH of the eluate from stage (vi), or of a fluid prepared by use of the eluate from stage (vi), to a pH between about 7 and about 8.

Embodiment 36

A method according to embodiment 35, wherein the stabilizing agent used in step (1) is a sugar, an alcohol or an alditol.

Embodiment 37

A method according to embodiment 36, wherein the stabilizing agent used in step (1) is a sugar, a $C_3$-$C_8$-alcohol or an alditol.

Embodiment 38

A method according to embodiment 37, wherein the stabilizing agent used in step (1) is a polyalcohol.

Embodiment 39

A method according to embodiment 37, wherein the stabilizing agent used in step (1) is selected from the group consisting of glycerol, propylene glycol, propan-1,3-diol, propyl alcohol and isopropyl alcohol.

Embodiment 40

A method according to embodiment 39, wherein the stabilizing agent used in step (1) is selected from the group consisting of glycerol, propylene glycol and propan-1,3-diol.

Embodiment 41

A method according to any of embodiments 38 to 40, wherein the stabilizing agent used in step (1) is added to a concentration of from about 5% (v/v) to about 50% (v/v).

Embodiment 42

A method according to embodiment 41, wherein the stabilizing agent used in step (1) is added to a concentration of from about 10% (v/v) to about 50% (v/v).

Embodiment 43

A method according to embodiment 42, wherein the stabilizing agent used in step (1) is added to a concentration of from about 10% (v/v) to about 20% (v/v).

Embodiment 44

A method according to any of embodiments 35 to 43, wherein the pH of the eluate from stage (vi), or of a fluid prepared by use of the eluate from stage (vi), is adjusted in step (2) to a pH between about 7 and about 8.

Embodiment 45

A method according to embodiment 44, wherein the pH of the eluate from stage (vi), or of a fluid prepared by use of the eluate from stage (vi), is adjusted in step (2) to a pH of about 7.5.

Embodiment 46

A method according to any of embodiments 9 to 45, wherein no precipitation step to produce a factor XIII polypeptide-containing precipitate is performed after step (vi).

Embodiment 47

A method according to any of embodiments 1 to 46, wherein the method further comprises a step of subjecting the eluate from the hydrophobic interaction chromatography, or a material prepared by use of the eluate from the hydrophobic interaction chromatography, to chromatography on an anion-exchange matrix.

Embodiment 48

A method according to any of embodiments 9 to 47, wherein the method further comprises a step of:
subjecting the eluate from stage (vi), or a fluid prepared by use of the eluate from stage (vi), to chromatography on a second anion-exchange chromatographic material, said chromatography comprising:
(vii) applying the eluate from stage (vi), or a fluid prepared by use of the eluate from stage (vi), to said second anion-exchange chromatographic material;
(viii) eluting unbound material from the second anion-exchange chromatographic material with buffer C, which buffer C is suitable for eluting material not bound to the second anion-exchange chromatographic material; and
(ix) eluting said factor XIII polypeptide from the second anion-exchange chromatographic material with buffer C', wherein buffer C' is suitable for eluting factor XIII polypeptides which bind to the second anion-exchange chromatographic material in step (viii).

Embodiment 49

A method according to embodiment 48, wherein buffer C and/or buffer C' comprises one or more stabilizing agents which are capable of increasing the stability of the factor XIII polypeptide.

Embodiment 50

A method according to embodiment 49, wherein buffer C and/or buffer C' comprises a stabilizing agent, which stabilizing agent is a sugar, an alcohol or an alditol.

Embodiment 51

A method according to embodiment 50, wherein buffer C and/or buffer C' comprises a stabilizing agent, which stabilizing agent is a sugar, a $C_3$-$C_8$-alcohol or an alditol.

Embodiment 52

A method according to embodiment 51, wherein buffer C and/or buffer C' comprises a stabilizing agent, which stabilizing agent is a polyalcohol.

Embodiment 53

A method according to embodiment 52, wherein buffer C and/or buffer C' comprises a stabilizing agent selected from the group consisting of glycerol, propylene glycol, propan-1, 3-diol, propyl alcohol and isopropyl alcohol.

Embodiment 54

A method according to embodiment 53, wherein buffer C and/or buffer C' comprises a stabilizing agent selected from the group consisting of glycerol, propylene glycol and propan-1,3-diol.

Embodiment 55

A method according to any of embodiments 52 to 54, wherein said stabilizing agent is present in a concentration of from about 5% (v/v) to about 50% (v/v).

Embodiment 56

A method according to embodiment 55, wherein said stabilizing agent is present in a concentration of from about 10% (v/v) to about 50% (v/v).

Embodiment 57

A method according to embodiment 56, wherein said stabilizing agent is present in a concentration of from about 10% (v/v) to about 20% (v/v).

Embodiment 58

A method according to embodiment 57, wherein said stabilizing agent is present in a concentration of about 10% (v/v).

Embodiment 59

A method according to embodiment 57, wherein said stabilizing agent is present in a concentration of about 20% (v/v).

Embodiment 60

A method according to any of embodiments 48 to 59, wherein buffer C and/or buffer C' has a pH of about 7.5.

Embodiment 61

A method according to any of embodiments 48 to 60, wherein the conductivity of the eluate from step (ix) containing the factor XIII polypeptide is adjusted to about 10 mS/cm.

Embodiment 62

A method according to any of embodiments 48 to 61, wherein the pH of the eluate from step (ix) containing the factor XIII polypeptide is adjusted to about 7.5.

Embodiment 63

A method according to any of embodiments 48 to 62, wherein no precipitation step to produce a factor XIII-containing precipitate is performed after step (ix).

Embodiment 64

A method according to any of embodiments 1 to 62, wherein no precipitation step to produce a factor XIII-containing precipitate is performed.

Embodiment 65

A method for purifying a factor XIII polypeptide from a biological material, the method comprising the step of subjecting the biological material to chromatography using a hydrophobic interaction chromatographic material, wherein said hydrophobic interaction chromatographic material is chosen among Phenyl Sepharose™ High Performance High Substitution, Source™ 15 Phe and Sepharose™ 6 Fast Flow High Substitution.

Embodiment 66

A method according to embodiment 65, wherein the factor XIII polypeptide is a recombinant factor XIII.

Embodiment 67

A method according to embodiment 65 or embodiment 66, wherein the factor XIII polypeptide is human factor XIII.

Embodiment 68

A method according to embodiment 65 or embodiment 66, wherein the factor XIII polypeptide is a dimer of A subunits.

Embodiment 69

A method according to embodiment 68, wherein the factor XIII polypeptide is a dimer of human A subunits.

Embodiment 70

A method according to any of embodiments 65 to 69, wherein the biological material is a biological fluid.

Embodiment 71

A method according to any of embodiments 65 to 70, wherein no precipitation step to produce a factor XIII-containing precipitate is performed.

Embodiment 72

A pharmaceutical composition comprising a factor XIII polypeptide prepared by use of a method according to any of embodiments 1 to 71.

Embodiment 73

A pharmaceutical composition according to embodiment 72, wherein the pharmaceutical composition is an aqueous composition and comprises 20% (v/v) propylene glycol.

Embodiment 74

A pharmaceutical composition according to embodiment 72, wherein the pharmaceutical composition is an aqueous composition and comprises 1.5% (w/v) sucrose and 3.5% (w/v) mannitol.

Embodiment 75

Use of a pharmaceutical composition according to any of embodiments 72 to 74 for reducing blood loss.

Embodiment 76

Use of a pharmaceutical composition according to any of embodiments 72 to 74 for the prevention of intraventricular haemorrhage in premature infants.

Embodiment 77

Use of a pharmaceutical composition according to any of embodiments 72 to 74 for reducing surgery-related blood loss in a patient during or after surgery.

Embodiment 78

Use of a pharmaceutical composition according to any of embodiments 72 to 74 for treating hemophilia A.

Embodiment 79

Use of a pharmaceutical composition according to any of embodiments 72 to 74 for treating hemophilia B.

Embodiment 80

Use of a pharmaceutical composition according to any of embodiments 72 to 74 for treating platelet disorders.

Embodiment 81

Use of a pharmaceutical composition according to any of embodiments 72 to 74 for treating von Willebrand's disease.

Embodiment 82

Use of a factor XIII polypeptide prepared by use of a method according to any of embodiments 1 to 71 for preparation of a pharmaceutical composition for use in reducing blood loss.

Embodiment 83

Use of a factor XIII polypeptide prepared by use of a method according to any of embodiments 1 to 71 for preparation of a pharmaceutical composition for prevention of intraventricular haemorrhage in premature infants.

Embodiment 84

Use of a factor XIII polypeptide prepared by use of a method according to any of embodiments 1 to 71 for preparation of a pharmaceutical composition for reducing surgery-related blood loss in a patient during or after surgery.

Embodiment 85

Use of a factor XIII polypeptide prepared by use of a method according to any of embodiments 1 to 71 for preparation of a pharmaceutical composition for treating hemophilia A.

Embodiment 86

Use of a factor XIII polypeptide prepared by use of a method according to any of embodiments 1 to 71 for preparation of a pharmaceutical composition for treating hemophilia B.

Embodiment 87

Use of a factor XIII polypeptide prepared by use of a method according to any of embodiments 1 to 71 for preparation of a pharmaceutical composition for treating platelet disorders.

Embodiment 88

Use of a factor XIII polypeptide prepared by use of a method according to any of embodiments 1 to 71 for preparation of a pharmaceutical composition for treating von Willebrand's disease.

The present invention is illustrated by the followed non-limiting examples.

EXAMPLES

Example 1

Disruption of Yeast Cells

A culture comprising cells of the yeast *Saccharomyces cerevisiae* expressing the amino acid sequence 1-731 of human factor XIII was centrifuged for 8 min. in a Sorvall SLA centrifuge at 6000 rpm at 4° C., and the cells were resuspended in freshly made buffer (20% by volume (v/v) propylene glycol, 20 mM Tris, 1 mM PMSF, pH 8.0) in an amount of 3 ml of buffer per gram of cell pellet. The suspension was then subjected to a pressure of 1.5 kBar at a temperature below 15° C. The resulting suspension was centrifuged for 30 min. in a Sorvall SLA centrifuge at 9000 rpm at 4° C., and the pH of the supernatant was adjusted to 8.0 with 1 M NaOH. The supernatant was then filtered on Advantec GF75 0.7 μm GF075090+ round filter MN GF5 0.4 μm 001201 art no. 415009 and kept at 4° C. until further use (in Example 2).

Example 2

First Anion-Exchange Chromatography Using Source™ 30Q

The conductivity of the filtered supernatant from Example 1 was adjusted to below 2 mS/cm by use of a freshly made buffer A (20% (v/v) propylene glycol, 20 mM Tris, 1 mM PMSF, pH 8.0). A Source™ 30Q matrix was equilibrated with 5 column volumes (cv) of buffer A, and a load corresponding to the amount of polypeptide produced by 1.3 g yeast cells was applied to the column. The column was washed with 7 cv of buffer A and then with 5 cv of 10% of the elution buffer (20% (v/v) propylene glycol, 20 mM Tris, 0.2 M NaCl, 1 mM PMSF, pH 8.0). Gradient elution was then performed, going from 10% elution buffer to 100% elution buffer over 25 cv followed by 5 cv of 100% elution buffer at a flow of 12 cv/hour. Fractions were collected from at about 30% elution buffer to at about 70% elution buffer. Analysis of factor XIII polypeptide-containing fractions was performed by HPLC (vide infra) using DEAE-NPR (TosoHaas, cat. no. 13075, 4.6×35 mm) and by SDS-PAGE on a NUpage 4-12% Bis/Tris Gel (Invitrogen) with MOPS running buffer under reductive conditions. Fractions containing factor XIII polypeptide were kept at approx. +4° C. in a refrigerator, or frozen at −80° C., until further use (in Example 3).

Example 3

Hydrophobic Interaction Chromatography Using Source™ 15Phe

One volume of a buffer containing 400 mM $K_2HPO_4$+400 mM $KH_2PO_4$ was added to the combined fractions containing factor XIII polypeptide from Example 2, and the pH was adjusted to 7.5 with NaOH. A Source™ 15Phe matrix was equilibrated with 4 cv of buffer B (100 mM $K_2HPO_4$, 100 mM $KH_2PO_4$, pH 7.5), and a load corresponding to approximately 2 mg/ml was applied to the column. The column was then washed with 4 cv of buffer B and then subjected to gradient elution going from buffer B to 100% elution buffer (5 mM $K_2HPO_4$, 5 mM $KH_2PO_4$, pH 7.5) over 20 cv followed by 2 cv of 100% elution buffer at a flow of 8 cv/h. Fractions were collected after elution of approximately 4 cv and until 18 cv. Analysis of factor XIII polypeptide-containing fractions was performed by HPLC (vide infra) using DEAE-NPR (Toso-Haas, cat. no. 13075, 4.6×35 mm) and by SDS-PAGE on a NUpage 4-12% Bis/Tris Gel (Invitrogen) with MOPS running buffer under reductive conditions. A ¼ volume of propylene glycol was immediately added to the pool of factor XIII polypeptide-containing fractions to a final concentration of 20% (v/v) propylene glycol, and the resulting pool was then kept at approx. +4° C. in a refrigerator, or frozen, until further use (in Example 5).

Example 4

Hydrophobic Interaction Chromatography Using Phenyl Sepharose™ High Performance High Substitution One volume of a buffer containing 400 mM $K_2HPO_4$+400 mM $KH_2PO_4$ was added to the combined fractions containing factor XIII polypeptide from Example 2, and the pH was adjusted to 7.5 with NaOH. A Phenyl Sepharose™ High Performance High Substitution matrix was equilibrated with 4 cv of buffer B (100 mM $K_2HPO_4$, 100 mM $KH_2PO_4$, pH 7.5), and a load corresponding to approximately 2 mg/ml was applied to the column. The column was then washed with 4 cv of buffer B and then subjected to gradient elution going from buffer B to 100% elution buffer (5 mM $K_2HPO_4$, 5 mM $KH_2PO_4$, pH 7.5) over 20 cv followed by 2 cv of 100% elution buffer at a flow of 8 cv/h. Fractions were collected after elution of approximately 10 cv and until 20 cv. Analysis of factor XIII polypeptide-containing fractions was performed by HPLC (vide infra) using DEAE-NPR (TosoHaas, cat. no. 13075, 4.6×35 mm) and by SDS-PAGE on a NUpage 4-12% Bis/Tris Gel (Invitrogen) with MOPS running buffer under reductive conditions. A ¼ volume of propylene glycol was immediately added to the pool of factor XIII polypeptide-containing fractions to a final concentration of 20% (v/v) propylene glycol, and the resulting pool was then kept at approx. +4° C., or frozen, until used in a procedure as described in Example 5.

Example 5

Second Anion-Exchange Chromatography Using Source™ 30Q

Alternative 1)

The pH of the pool of factor XIII polypeptide-containing fractions from Example 3 was adjusted to 7.5, and buffer C (20% (v/v) propylene glycol, 10 mM glycyl-glycine, pH 7.5) was added to a conductivity of below 2 mS/cm. A Source™ 30Q matrix was equilibrated with 5 cv of buffer C, and then a load corresponding to 5 mg/ml gel was applied to the column. The column was then washed with 8 cv of buffer C, and a buffer containing 67% buffer C and 33% elution buffer (20% (v/v) propylene glycol, 10 mM glycyl-glycine, 0.5 M NaCl, pH 7.5) was used to elute the factor XIII polypeptide in small fractions. The conductivity of the pool containing the factor XIII polypeptide fractions was adjusted to about 10 mS/cm with a buffer containing 20% (v/v) propylene glycol, 10 mM glycyl-glycin, 2 M NaCl (pH 7.5).

Example 6

Second Anion-Exchange Chromatography Using Source™ 30Q

Alternative 2

The pH of the pool of factor XIII polypeptide-containing fractions from Example 3 was adjusted to 7.5, and buffer D (1.5% weight per volume (w/v) sucrose, 3.5% (w/v) mannitol, 10 mM glycyl-glycine, pH 7.5) was added to a conductivity of below 2 mS/cm. A Source™ 30Q matrix was equilibrated with 5 cv of buffer D, and then a load corresponding to 5 mg/ml gel was applied to the column. The column was then washed with 8 cv of buffer D, and a buffer containing 67% buffer D and 33% elution buffer (1.5% (w/v) sucrose, 3.5% (w/v) mannitol, 0.5 M NaCl, pH 7.5) was used to elute the factor XIII polypeptide in small fractions. The conductivity of the pool containing the factor XIII polypeptide fractions was adjusted to about 10 mS/cm with a buffer containing 1.5% (w/v) sucrose, 3.5% (w/v) mannitol, 2 M NaCl (pH 7.5).

HPLC Analysis Procedure

High-Performance Liquid Chromatography (HPLC; referred to in Examples 2-4, above) was performed using DEAE-NPR column matrix material from TosoHaas (cat. No. 13075, 4.6×35 mm) and employing buffers as follows:
Buffer I: 20 mM $K_2HPO_4$, pH 8.0 (adjusted with HCl)
Buffer II: 20 mM $K_2HPO_4$, 0.4 M KCl, pH 8.0 (adjusted with HCl).

Equilibration of the column was carried out using a mixture of 95% (v/v) Buffer I with 5% (v/v) Buffer II for 2.5 minutes (flow rate 0.5 ml/min.).

Elution of the column took place using a gradient going from 95% Buffer I/5% Buffer II to 60% Buffer I/40% Buffer II over a period of 17 minutes (flow rate 0.5 ml/min.).

Regeneration of the column was performed by washing with 100% Buffer II for 1.4 minutes (flow rate 0.5 ml/min.). Each day before use of the column it was found advantageous to inject 100 it 0.2 M NaOH followed by 100 µl 1 M $K_2HPO_4$, pH 8.0, onto the column before performing a new cycle of equilibration, elution and regeneration. 1 M citric acid (pH 3.0) may alternatively be employed.

The detection wavelength employed was 220 nm.

Samples of from 2 to 30 μg were loaded onto the column; by four-fold dilution of samples with water it was possible to load up to 30 μg of sample irrespective of injection volume up to 100 μl. The use of greater injection volumes and higher sample loadings was not examined.

Examples of Results from 3 Purifications Carried Out According to Examples 1, 2, 3 and 5

|  | Fermentation No. | | |
| --- | --- | --- | --- |
|  | H913 | H932 | H933 |
| Cell mass/gram | 1057 | 1630 | 1830 |
| Yield (mg) after source 30Q (Ex. 2) | 529 | 699 | 977 |
| Purity (HPLC %) after source 30Q (Ex. 2) | 79 | 84 | 64 |
| Yield (mg) after source15phe (Ex. 3) | 514 | 314 | 638 |
| Yield (%) after source15phe (Ex. 3) | 97 | 45 | 65 |
| Purity (HPLC) after source15phe (Ex. 3) | 90 | 93 | 82 |
| Yield (mg) after concentration on Source30Q, (UV), (Ex. 5) | 363 | 270 | 456 |
| Yield after concentration on Source30Q (%) (Ex. 5) | 70.6 | 86 | 71 |
| Purity (HPLC) after concentration on Source30Q (Ex. 5) | 90.2 | 91.5 | 86 |

The invention claimed is:

1. A method for purifying a factor XIII polypeptide from a biological material comprising subjecting the biological material to sequential chromatography on an anion-exchange matrix and a hydrophobic interaction matrix wherein no precipitation step to produce a factor XIII polypeptide-containing precipitate is performed, and wherein chromatography on an anion-exchange matrix is performed with a stabilizing agent selected from the group consisting of propylene glycol, propan-1,3-diol, propyl alcohol, and isopropyl alcohol.

2. A method according to claim 1, wherein the factor XIII polypeptide is a recombinant factor XIII.

3. A method according to claim 2, wherein the factor XIII polypeptide is human factor XIII.

4. A method according to claim 2, wherein the factor XIII polypeptide is a dimer of A subunits.

5. A method according to claim 4, wherein the factor XIII polypeptide is a dimer of human A subunits.

6. A method according to claim 1, wherein the biological material is a biological fluid.

7. A method according to claim 6, wherein the biological fluid is the supernatant of a cell lysate.

8. A method according to claim 7, wherein the biological fluid is the supernatant of a yeast cell lysate.

* * * * *